United States Patent [19]

Fiddian-Green

[11] Patent Number: 5,788,631
[45] Date of Patent: *Aug. 4, 1998

[54] HOLLOW VISCUS AND SOLID ORGAN TONOMETRY

[75] Inventor: Richard Guy Fiddian-Green, One Marlborough, Mass.

[73] Assignee: Instrumentarium Corporation, Finland

[*] Notice: The term of this patent shall not extend beyond the expiration date of Pat. No. 5,174,290.

[21] Appl. No.: 608,714

[22] Filed: Feb. 29, 1996

Related U.S. Application Data

[63] Continuation of Ser. No. 445,071, May 19, 1995, Pat. No. 5,526,809, which is a continuation of Ser. No. 279,000, Jul. 22, 1994, abandoned, which is a continuation of Ser. No. 34,596, Mar. 22, 1993, abandoned, which is a continuation of Ser. No. 719,097, Jun. 20, 1991, abandoned, which is a continuation of Ser. No. 513,026, Apr. 24, 1990, abandoned, which is a continuation of Ser. No. 237,288, Aug. 26, 1988, abandoned, which is a continuation-in-part of Ser. No. 233,888, Aug. 17, 1988, which is a continuation of Ser. No. 120,720, Nov. 6, 1987, abandoned, which is a continuation of Ser. No. 13,552, Feb. 11, 1987, abandoned, which is a continuation of Ser. No. 833,287, Feb. 27, 1986, Pat. No. 4,643,192, which is a continuation of Ser. No. 360,718, Mar. 22, 1982, abandoned.

[51] Int. Cl.⁶ ............................................. A61B 5/00
[52] U.S. Cl. .............................................. 600/309
[58] Field of Search .................................. 128/632, 635, 128/691, 672, 673, 736, 748, 749, 774, 778, 780, 782

[56] References Cited

U.S. PATENT DOCUMENTS

| | | |
|---|---|---|
| 3,043,309 | 7/1962 | McCarthy . |
| 3,339,552 | 9/1967 | Aillon . |
| 3,395,710 | 8/1968 | Stratton et al. . |
| 3,437,088 | 4/1969 | Bielinski . |
| 3,480,003 | 11/1969 | Crites . |
| 3,658,053 | 4/1972 | Fergusson et al. . |
| 3,734,094 | 5/1973 | Calinog . |
| 3,794,041 | 2/1974 | Frei et al. . |
| 3,983,879 | 10/1976 | Todd . |
| 4,003,705 | 1/1977 | Buzza et al. . |
| 4,063,561 | 12/1977 | McKenna . |
| 4,120,292 | 10/1978 | LeBlanc, Jr. et al. . |

(List continued on next page.)

FOREIGN PATENT DOCUMENTS

89-03659  8/1989  WIPO .

OTHER PUBLICATIONS

Ali, J. et al., "The Cardiorespiratory Effects of Increased Intra-Abdominal Pressure in Diaphragmatic Rupture," *J. Trauma* 33:233–239 (1992).

Anzivino, M.J. et al., "Elevated Systemic to Intramucosal Stomach Wall pH-GAP in Patients with Sepsis," *Chest* 98(2) (1990) Suppl.

Badgwell, J. M. et al., "End-Tidal Carbon Dioxide Pressure in Neonates and Infants Measured by Aspiration and Flow-Through Capnography," *J. Clin. Monit.* 7:285–288 (1991).

(List continued on next page.)

*Primary Examiner*—John P. Lacyk
*Attorney, Agent, or Firm*—Harness, Dickey & Pierce, P.L.C.

[57] ABSTRACT

Ischemia in a hollow internal organ can be detected in its incipient stages by obtaining a $CO_2$ sample from within the organ of interest, measuring the partial pressure of $CO_2$ sample, measuring the bicarbonate concentration of an arterial blood sample, and on the basis of these two measurements calculating the pH of the wall of the organ. The value of the pH is an indicator of the onset of ischemia in the organ. The $CO_2$ sample is obtained by a novel catheter, multiple embodiments of which are disclosed. Also disclosed is a method for determining the vitality or adequacy of oxygenation of the whole body, or a solid internal organ, by the measurement of the pH of venous blood.

3 Claims, 3 Drawing Sheets

U.S. PATENT DOCUMENTS

| | | |
|---|---|---|
| 4,173,981 | 11/1979 | Mortensen . |
| 4,176,659 | 12/1979 | Rolfe . |
| 4,187,856 | 2/1980 | Hall et al. . |
| 4,214,593 | 7/1980 | Imbruce et al. . |
| 4,221,567 | 9/1980 | Clark et al. . |
| 4,223,513 | 9/1980 | Elder et al. . |
| 4,224,377 | 9/1980 | Grams . |
| 4,259,960 | 4/1981 | Taylor . |
| 4,265,249 | 5/1981 | Schindler et al. . |
| 4,273,636 | 6/1981 | Shimada et al. . |
| 4,304,239 | 12/1981 | Perlia . |
| 4,338,174 | 7/1982 | Tamura . |
| 4,381,011 | 4/1983 | Somers, III . |
| 4,384,586 | 5/1983 | Christiansen . |
| 4,423,739 | 1/1984 | Passaro et al. . |
| 4,432,366 | 2/1984 | Margules . |
| 4,480,190 | 10/1984 | Burough et al. . |
| 4,497,324 | 2/1985 | Sullivan et al. . |
| 4,516,580 | 5/1985 | Polanyi . |
| 4,534,825 | 8/1985 | Koning et al. . |
| 4,576,590 | 3/1986 | Fiddian-Green . |
| 4,580,560 | 4/1986 | Straith . |
| 4,583,969 | 4/1986 | Mortensen . |
| 4,596,931 | 6/1986 | Ehnholm et al. . |
| 4,610,656 | 9/1986 | Mortensen . |
| 4,643,192 | 2/1987 | Fiddian-Green . |
| 4,671,287 | 6/1987 | Fiddian-Green . |
| 4,727,730 | 3/1988 | Boiarski et al. . |
| 4,738,668 | 4/1988 | Bellotti et al. . |
| 4,774,956 | 10/1988 | Kruse et al. . |
| 4,784,660 | 11/1988 | Fischell . |
| 4,790,328 | 12/1988 | Young . |
| 4,792,330 | 12/1988 | Lazarus et al. . |
| 4,809,710 | 3/1989 | Williamson . |
| 4,850,958 | 7/1989 | Berry et al. . |
| 4,859,858 | 8/1989 | Knodle et al. . |
| 4,859,859 | 8/1989 | Knodle et al. . |
| 4,873,990 | 10/1989 | Holmes et al. . |
| 4,907,166 | 3/1990 | Coreman et al. . |
| 4,914,720 | 4/1990 | Knodle et al. . |
| 4,966,578 | 10/1990 | Baier et al. . |
| 4,981,470 | 1/1991 | Bombeck, IV . |
| 4,998,527 | 3/1991 | Meyer . |
| 5,002,055 | 3/1991 | Merki et al. . |
| 5,042,522 | 8/1991 | Coreman et al. . |
| 5,067,492 | 11/1991 | Yelderman et al. . |
| 5,095,913 | 3/1992 | Yelderman et al. . |
| 5,158,083 | 10/1992 | Sacristan et al. . |
| 5,167,237 | 12/1992 | Rabin et al. . |
| 5,174,290 | 12/1992 | Fiddian-Green . |
| 5,186,172 | 2/1993 | Fiddian-Green . |

OTHER PUBLICATIONS

Bagley, N.A. et al., "Urodynamic Evaluation of Voluntary Detrusor Response in Healthy Subjects," *Arch. Phys. Med. Rehabil.* 66:160–163 (1985).

Barbalias, G.A. et al., "Rectal Pressure Measurements and Intra-Abdominal Pressure Changes".

Barnes, G.E. et al., "Cardiovascular Responses to Elevation of Intra-Abdominal Hydrostatic Pressure," *Am. J. Physiol.* 48:R208–R213 (1985).

Bass, B.L., et al., "Intraluminal $pCO_2$: A reliable Indicator of Intestinal Ischemia," *J. Surg. Res.* 39:351–360 (1985).

Bergofsky, E.A., "Determination of Tissue $O_2$ Tensions by Hollow Visceral Tonometers: Effect of Breathing in Enriched $O_2$ Mixtures" *J. Clin. Invest.* 43:193–200 (1964).

Boda, D. et al., "Gastrotonometry an Aid to the Control of Ventilation During Artificial Respiration," *Lancet* Jan. 24, 1959 pp. 181 and 182.

Bradley, S.E. et al., "The Effect of Increased Intra-Abdominal Pressure on Renal Function in Man," *J. Clin. Invest.* 26:1010–1022 (1947).

Brantigan, J.W. et al., "A Teflon Membrane for Measurement of Blood and Intramyocardial Gas Tensions by Mass Spectroscopy," *J. Applied Physiol.* 32:276–282 (1972).

Bryant, T.N. et al., "Indirect Monitoring and Analysis of Truncal Stress Over Extended Time Periods," *J. Biomed. Eng.* 8:172–174 (1986).

Buchler, B. et al., "Effects of Pleural Pressure and Abdominal Pressure on Diaphragmatic Blood Flow," *J. Applied Physiol.* 58:691–697 (1985).

Burchard, K.W. et al., "Positive and Expiratory Pressure with Increased Intra-Abdominal Pressure," *SGO* 161:313–318 (1984).

Cadwell, C.B. et al., "Evaluation of Intra-Abdominal Pressure and Renal Hemodynamics," *Current Surg.* 43:495–498 (1986).

Cadwell, C.B. et al., "Changes in Visceral Blood Flow with Elevated Intraabdominal Pressure," *J. Surg. Res.* 43:14–20 (1987).

Calloway, D.H., "Gas in the Alimentary Canal," Chapter 137 in *Handbook of Physiology—Alimentary Canal,* V:2839–2859.

Celoria, G. et al., "Oliguria from High Intra-Abdominal Pressure Secondary to Ovarian Mass," *Crit. Care Med.* 15:78–79 (1987).

Cerabona, T. et al., "Urinary Bladder Measurements of Intra-Abdominal Pressure (IAP) in Ascitic Cirrhotics Predictive of Hemodynamic and Renal Function," *Crit. Care Med.* 16:431 (1988).

Collee, G.G. et al., "Bedside Measurement of Intra-Abdominal Pressure (IAP) Via an Indwelling Naso–Gastric Tube: Clinical Validation of the Technique," *Intensive Care Med.* 19:478–480 (1993).

Cresswell, A.G. et al., "Observations on Intra-Abdominal Pressure and Patterns of Abdominal Intra-Muscular Activity in Man," *Acta. Physiol. Scand.* 144:409–418 (1992).

Cresswell, A. G., et al., "Intra-Abdominal Pressure and Patterns of Abdominal Muscle Activation in Isometric Trunk Flexion and Extension," *Abstracts—International Society of Biomechanics XII Congress* p. 998 (1989).

Cullen, D.J. et al., "Cardiovascular, Pulmonary, and Renal Effects of Massively Increased Intra-Abdominal Pressure in Critically Ill Patients," *Crit. Care Med.* 17:118–121 (1989).

Daly, R.C. et al., "Abdominal Reexploration for Increased Intra-Abdominal Pressure and Acute Oliguric Renal Failure," *Contemp. Surg.* 35:11–18 (1989).

Dawson, A.M., "Small Bowel Tonometry: Assessment of Small Mucosal Oxygen Tension in Dog and Man," *Nature* 206:943–944 (1965).

Diebel, L.N. et al., "Effect of Increased Intra-Abdominal Pressure on Mesenteric Arterial and Intestinal Mucosal Blood Flow," *J. Trauma* 33(1):45–49 (1992).

Diebel, L. et al., "Effect of Intra-Abdominal Pressure on Abdominal Wall Blood Flow," *Am. Surg.* 58:573–576 (1992).

Diebel, L.N. et al., "Effect on Increased Intra-Abdominal Pressure on Hepatic Arterial, Portal Venous, and Hepatic Microcirculatory Blood Flow," *J. Trauma* 33:279–283 (1992).

Ducas, J. et al., "Thoracicoabdominal Mechanics During Resuscitation Maneuvers," *Chest* 84/4 (1983).

Elder, J.B. et al., "Intragastric $PCO_2$ in Man and Calculated Gastric Bicarbonate Concentrations: Effect of Carbenoxolone Sodium," *Carbenoxolone Effect on Intragastric $PCO_2$ and $HCO_3$* pp. 19–25 (1980).

Emerson, H., "Intra–Abdominal Pressures," *Arch. Int. Med.* 7:754–784 (1911).

Fairback, J.C. et al., "Intraabdominal Pressure Rise During Weight Lifting as an Objective Measure of Low–Back Pain," *Spine* 5(2):179–184 (1980).

Fantl, J. et al., "Efficacy of Bladder Training in Older Women with Urinary Incontinence," *JAMA* 265(5):609–613 (1991).

Fiddian–Green presentation "Advances in ICU Monitoring Techniques," Oct. 25–29, 1992.

Fiddian–Green, R.G., "pH–Gap: A Measurement for Estimating the Presence or Absence of Intestinal Mucosal Ischemia Independently of Disturbances in Systemic Acid Base Balance," (Abstract) ESSR Meeting in Finland (May 23–26, 1993).

Fiddian–Green, R.G., "Should Measurement of Tissue pH and $PO_2$ be Included in the Routine Monitoring of Intensive Care Unit Patients?" *Crit. Care Med.* 19:141–143 (1991).

Fietsam, R. et al., Intra–Abdominal Compartment Syndrome as a Complication of Ruptured Abdominal Aortic Aneurysm Repair, *Am. Surg.* 55:396–402 (1989).

Fischer, M., Raised Intra–Abdominal Pressure, Renal Failure and the Bumble Bee, *Int. Care Med.* 16:285–286 (1990).

Guazzi, M. et al., "Negative Influences of Ascites on the Cardiac Function of Cirrhotic Patients," *Am. J. Med.* 59:165–170 (1975).

Gutierez, G. et al. "Gastric Intramucosal pH as a Therapeutic Index of Tissue Oxygenation in Critically Ill Patients" *The Lancet* 339:195–199 (1992).

Guyton, A.C. et al., "Quantitative Aspects of the Collapse Factor in Relation to Venous Return," *Am. J. Physiol.* 177:523–527 (1954).

Hamilton, J.D. et al., "Observations upon Small Gut Mucosal $pO_2$ and $pCO_2$ in Anesthetized Dogs," *Gastroenterology* 55:52–60 (1968).

Hargreaves, D.M., "Raised Intra–Abdominal Pressure and Renal Failure," *Anaesthesia* 46:796 (1991).

Harman, K.P. et al., "Elevated Intra–Abdominal Pressure and Renal Function," *Ann. Sur.* 196:594–597 (1982).

Higgins, J.R. et al., "Tension Pneumoperitoneum: A Surgical Emergency," *Br. J. Hos. Med.* pp. 160–161 (1988).

Hoffman, R.A. et al., "End–Tidal Carbon Dioxide in Critically Ill Patients during Changes in Mechanical Ventilation," *Am. Ref. Respir. Dis.* 140:1265–1268 (1989).

Hunt, T.K. "A New Method of Determining Tissue Oxygen Tension," *Lancet* 1370–1371 (1964).

Iberti, T.J. et al., "Determination of Intra–Abdominal Pressure Using a Transurethral Bladder Catheter: Clinical Validation of the Technique," *Anesthesiology* 70:47–50 (1989).

Jacques, T., et al., "Improvement of Renal Function after Relief of Raised Intra–Abdominal Pressure due to Traumatic Retroperitoneal Haematoma," *Anaesth. Intens. Care.* 16:478–494 (1988).

Jellinek, H. et al., "Arterial to End–Tidal $CO_2$ Tension Difference After Bilateral Lung Transplantation," *Crit. Care Med.* 21(7):1035–1040 (1990).

Kaback, K. et al. "Letters JAMA" *JAMA* 254:1035 (1985).

Kashtan, J. et al., "Haemodynamic Effects of Increased Abdominal Pressure," *J. Surg. Res.* 30:249–255 (1981).

Kelly, K. et al., "A Simple Non–Invasive Technique to Measure Intra–Abdominal Pressure," *Crit. Care* p. 366 (1987).

Kelly, K.M. et al., "A Simple Non–Invasive Technique to Measure Intra–Abdominal Pressure," (Abstracts) p. 371.

Kivilaakso, E., et al. "Gastric Blood Flow, Tissue Gas Tension and Microvascular Changes During Hemorrhage––Induced Stress Ulceration in the Pig," *Am. J. Surg.* 143:322–330 (1982).

Kivisaari, J. et al., "Use of Silastic Tube and Capillary Sampling Technic in the Measurement of Tissue $PCO_2$ and $PCO_2$," *Am. J. Surg.* 125:623–6627 (1973).

Kram, H.B. et al., "Noninvasive Measurement of Tissue Carbon Dioxide Tension Using a Fiberoptic Conjunctival Sensor: Effects of Respiratory and Metabolic Alkalosis and Acidosis," *Crit. Care Med.* 16:280–284 (1988).

Kron, I.L. et al., "The Measurement of Intra–Abdominal Pressure as a Criterion for Abdominal Re–Exploration," *Ann. Surg.* 199:28–30 (1984).

Lacey, S.R., et al., "The Relative Merits of Various Methods of Indirect Measurement of Intraabdominal Pressure as a Guide to Closure of Abdominal Wall Defects," *J. Ped. Surg.* 22(12):1207–1211 (1987).

Landers, B.R. et al., "Response of Porcine Lower Esophageal Sphincter to Increasing Intraabdominal Pressure," *Dig. Dis. Sci.* 32:272–279 (1987).

Lawson, D. et al., "Stability and Long–Term Durability of Raman Spectroscopy," *J. Clin. Monit.* 9:241–151 (1993).

Lenz, G. et al., "Capnometry for Continuous Postoperative Monitoring of Nonintubated, Spontaneously Breathing Patients," *J. Clin. Monit.* 7:245–248 (1991).

Leon, A. et al., "Septic Shock: Does Gastric Mucosal Tonometry Assess Tissue Oxygenation?" 79(3A) (1993).

Le Roith, D. et al., "The Effect of Abdominal Pressure on Plasma Antidiuretic Hormone in the Dog," *J. Sur. Res.* 32:65–69 (1982).

Luiz, T. et al., "Veranderungen der Ventilation Wahrend Laparoskopischer Cholezystektomie," *Anaesthesist* 41:520–529 (1992).

Lumsden, T. et al., "The PB3300 Intraarterial Blood Gas Monitoring System," *J. Clin. Monit.* 10(1):59–66 (1994).

Martinez–Pellus, A.E. et al., "Can Selective Digestive Decontamination Avoid the Endotoxemia and Cytokine Activation Promoted by Cardiopulmonary Bypass?" *Crit. Care Med.* 21:1684–1691 (1993).

McCarthy, T.A., "Validity of Rectal Pressure Measurements as Indication of Intra–Abdominal Pressure Changes During Urodynamic Evaluation," *Urology* 6:657–660 (1982).

McGee, Lemuel et al., "The Carbon Dioxide Tension and Acid–Base Balance of Jejunal Secretions in Man," 893–904 (1941).

McIver, M.A. et al., "Gaseous Exchange Between the Blood and the Lumen of the Stomach and Intestines," *Am. J. Physiol.* 76(1):92–111 (1926).

Motew, M. et al., "Cardiovascular Effects and Acid–Base and Blood Gas Changes during Laparoscopy," *Am. J. Obstet, Gynecol.* 115:1002–1012 (1972).

Nielsen, J.R. et al., "The Absorption Laws for Gases in the Infra–Red" *Rev. Modern Physics.* 16(3&4):307–324 (1944).

Niemczyk, T.M. et al., "Multichannel Raman Spectroscopy Tackles Industrial Problems," *Laser Focus World* Mar:85, 86, 90, 92, 95, 97 and 98 (1993).

Noc, M. et al., "Comparison of Gastric Luminal and Gastric Wall $PCO_2$ Duriing Hemorrhagic Shock," *Cir. Shock* 40:194–199 (1993).

Nordin, M. et al., "Intra-Abdominal Pressure Measurements Using a Wireless Radio Pressure Pill and Two Wire Connected Pressure Transducers: A Comparison," *Scand. J. Rehab. Med.* 16:139–146 (1984).

O'Leary M.J. et al., "Acute Renal Failure in Association with Pneumatic Antishock Garment and with Tense Ascites," *Anesthesia* 46:326–327 (1991).

Overholt, R.H., "Intraperitoneal Pressure," *Arch. Surg.* 22(5):691–703 (1931).

Paulus, D.A., "Capnography," *Int'l. Anes. Clin.* 27(3):167–174 (1989).

Platell, C.F. et al., "Impaired Renal Function Due to Raised Intraabdominal Pressure," *Intensive Care Med.* 16:328–329 (1990).

Raemer, D.B. et al., "Variation in $PCO_2$ between Arterial Blood and Peak Expired Gas during Anesthesia," *Anest. Analg.* 62:1065–1069 (1983).

Raemer, D.B. et al., "Monitoring Anesthetic and Respiratory Gases," Chapter 14 *Monitoring in Anesthesia and Critical Care Medicine* pp. 373–386.

Raemer, D.B. et al., "Accuracy of End–Tidal Carbon Dioxide Tension Analyzers," *J. Clin. Monit.* 7(2):195–208 (1991).

Richards, W.O. et al., "Acute Renal Failure Associated with Increased Intra-Abdominal Pressure," *Ann. Surg.* 197:183–187 (1983).

Ring, J.C. et al., "Effects of Acute Tense Abdominal Distention on Regional Blood Flow and Renal Function," *Critical Care Med.* 12:222 (1984).

Rippe M.D., J.M., *Medicine* 2nd ed. pp. 210–214.

Rodrigues, A.A. et al., "Therapeutic Exercise in Chronic Neck and Back Pain," *Arch. Phys. Med. Rehab.* 73:870–875 (1992).

Rowen, D. et al., "An Investigation of Bladder–Urethral Function by Pressure–Flow Studies," *BioMed Eng.* 304–308 (1972).

Roy, J. et al., "An Improved Nasal Prong Apparatus for End–Tidal Carbon Dioxide Monitoring in Awake, Sedated Patients," *J. Clin. Monit.* 7(3):249–252 (1991).

Rune, S.J. et al., "Carbon Dioxide Tensions in the Proximal Part of the Canine Gastrointestinal Tract," *Gastroenterology* 56:758–762 (1969).

Rune, S.J., "Acid–Base Parameters of Duodenal Contents in Man," *Gastroenterology* 62:533–539 (1972).

Salzman, A.L. et al., "Air Tonometry: A New Method for Determination of Gastrointestinal Mucosal $PCO_2$," *Crit. Care Med.* 21(4):S202 (1993).

Savino, J.A. et al., "Manipulation of Ascitic Fluid Pressure in Cirrhotics to Optimize Hemodynamic and Renal Function," *Ann. Surg.* 208:504–511 (1988).

Scannell, G. et al., "Tissue Oximetry in Hemorrhagic Shock and Resuscitation: Gastric But not Rectal Submucosal $pO_2$ Correlates with Gut Translocation," *Crit. Care Med.* 22:A187 (1993) (abstract).

Schwarz, C. et al., "Sodium–Taurocholate–Induced Acute Necrotizing Pancreatitis does not Affect Jejunal Oxygenation in Pigs," *Crit. Care Med.* 22:135–141 (1994).

Severinghaus, J.W. et al., "Correction Factors for INfrared Carbon Dioxide Pressure Broadening by Nitrogen, Nitrous Oxide and Cyclopropane," *Anesthesiology* 22(3):429–432 (1961).

Shafik, A. et al., "Dynamic Study of Rectal Detrusor Activity a Defecation," *Digestion* 49:167–174 (1991).

Shafik, A., "Straining Urethral Reflex: Description of a Reflex and its Clinical Significance," *Acta. Nat.* 140:104–107 (1991).

Shafik, A., "Esophago–Rectal Reflex:Description and Clinical Significance," *Int. Surg.* 78:83–85 (1993).

Shafik, A., "Straining Puborectalis Reflex: Description and Significance of a 'New' Reflex," *Anatomical Record* 229:281–284 (1991).

Shelly, M.P. et al., "Haemodynamic Effects Following Surgical Release of Increased Intra–Abdominal Pressure," *Br. J. Anaesth.* 59:800–805 (1987).

Shenasky, J.H. et al., "The Renal Haemodynamic and Functional Effects of External Counterpressure," *Surg. Gynecol. Obstet.* 134:253–258 (1972).

Siesjo, B.K., "A Method for Continuous Measurement of the Carbon Dioxide Tension on the Cerebral Cortex," *Acta Physiol. Scand.* 51:297–313 (1961).

Sloan, S. et al., "Determinants of Gastroesophageal Junction Incompetence: Hiatal Hernia, Lower Esophageal Sphincter, or Both?," *Am. College of Phys.* 117:977–982 (1992).

Smith, J.H. et al., "Reversal of Post–Operative Anuria by Decompressive Celiotomy," *Arch. Int. Med.* 145:553–554 (1985).

Smith–Wright, D.L. et al., "The Hemodynamic Effects of Dopamine and/or Volume Expansion in Acute Tense Abdominal Distention," *Crit. Care Med.* 270 (1985).

Starlinger, M. et al., "$H^+$ Back Diffusion Stimulating Gastric Mucosal Blood Flow in the Rabbit Fundus," *Surgery* 89:232–236 (1981).

Stock, M.C., "Noninvasive Carbon Dioxide Monitoring: Capnography," *Crit. Care Clin.* 4(3):511–526 (1988).

Stone, H.H. et al., "Renal Decapsulation in the Prevention of Post–Ischemic Oliguria," *Ann. Surg.* 186:343–355 (1977).

Sussman, A.M. et al., "Effect of Positive End–Expiratory Pressure on Intra–Abdominal Pressure," *South Med. J.* 84:697–700 (1991).

Tang, W. et al., "Gastric Intramural $PCO_2$ is Highly Correlated with Gastric Blood Flow During Both Menorrhagic and Anaphylactic Shock," *Crit. Care Med.* A108 (1994).

Thompson, D.G., et al., "Normal Patterns of Human Upper Small Bowel Motor Activity Recorded by Prolonged Radiotelemetry," *GUT* 21:500–506 (1980).

van Gool, J.D. et al., "Measurement of Intravesical and Rectal Pressures Simultaneously with Electromyography of Anal Sphincter in Children with Myelomeningocele," *Develop. Med. Child Neurol.* 18:287–301 (1976).

Vurek, G.G. et al., "A Fiber Optic $PCO_2$ Sensor," *Annal. Biomed. Eng.* 2:499–510 (1993).

Walton, D.M. "Continuous Monitoring of Blood pH, $PCO_2$ and $PO_2$ in Clinical Practice," Fifth ISA Biomedical Sciences Instrumentations Supposium, Denver, CO, May 1970 pp. 155–158.

Westenskow, D.R. et al., "Clinical Evaluation of a Raman Scattering–Multiple Gas Analyzer for the Operating Room," *Anesthesiology* 70:350–355 (1989).

Westenskow, D.R. et al., "Raman Scattering for Respiratory Gas Monitoring in the Operating Room: Advantages, Specifications, and Future Advances," *Biomed. Instru. Tech.* Nov./Dec.:485–489 (1989).

Westenskow, D.R. et al., "Can the Raman Scattering Analyzer Compete with Mass Spectrometers: An Affirmative Reply," *J. Clin. Monit.* 5(1):34–36 (1989).

HOLLOW VISCUS AND SOLID ORGAN TONOMETRY

This is a continuation of U.S. patent application Ser. No. 08/445,071, filed May 19, 1995 (now U.S. Pat. No. 5,526,809), which is a continuation of U.S. patent application Ser. No. 08/279,000, filed Jul. 22, 1994 (Abandoned), which is a continuation of U.S. patent application Ser. No. 08/034,596, filed Mar. 22, 1993 (Abandoned), which is a continuation of U.S. patent application Ser. No. 07/719,097, filed Jun. 20, 1991 (Abandoned), which is a continuation of U.S. patent application Ser. No. 07/513,026, filed Apr. 24, 1990 (Abandoned), which is a continuation of U.S. patent application Ser. No. 07/237,288, filed Aug. 26, 1988 (Abandoned), which is a continuation-in-part of U.S. patent application Ser. No. 07/233,888, filed Aug. 17, 1988 (Abandoned), which is a continuation of U.S. patent application Ser. No. 07/120,720, filed Nov. 6, 1987 (Abandoned), which is a continuation of U.S. patent application Ser. No. 07/013,552, filed Feb. 11, 1987 (Abandoned), which is a continuation of U.S. patent application Ser. No. 06/833,287, filed Feb. 27, 1986 (now U.S. Pat. No. 4,643,192), which is a continuation of U.S. patent application Ser. No. 06/360,718, filed Mar. 22, 1982 (Abandoned).

BACKGROUND AND SUMMARY OF THE INVENTION

This invention relates to medical diagnostic equipment and methods and is particularly concerned with hollow viscus tonometry, as well as determining the vitality or adequacy of oxygenation of the body or solid internal body organs.

Stress ulceration and intestinal ischemia are two serious problems that plague physicians involved in the management of patients in intensive care units. Intestinal ischemia, in particular, has an insidious onset and may not be detected until days after the intestine has become gangrenous. A delay in the diagnosis of intestinal ischemia may have devastating consequences for a patient. The availability of means for early diagnosis and management of patients with these problems would have immediate applicability in all intensive care units, especially where the procedure can be conveniently conducted with reasonable safety and reliability.

It has been established that a fall in the intramuscosal pH may precede the development of stress ulceration. One aspect of the invention involves the discovery, in the laboratory, that a fall in intrasmucosal pH also occurs within minutes of inducing intestinal ischemia in dogs. The fall in pH in intestinal mucosal, and hence the liklihood of stress ulceration or ischemia, can be reliably calculated from a $pCO_2$ (partial pressure of $CO_2$) in luminal fluid and the bicarbonate concentration in arterial blood. The method of calculating the pH in intestinal muscosal tissue, pursuant to principles of the invention, has been validated by direct measurements under a variety of conditions simulating clinical problems. A correlation coefficient in the order of 0.92 to 0.95 has been obtained in each of sixteen dogs. It will be readily recognized that the validity of the procedure is inherently extensible to humans.

To measure the $pCO_2$ in the lumen of the gut it is necessary to obtain a sample of fluid that has been in contact with the wall of the gut for a certain time period, usually at least half an hour. It is difficult to aspirate fluid from the lumen of the gut with any consistency, for any fluid instilled into the lumen passes into distal and proximal regions. It is much easier to obtain samples from the stomach, but samples obtained from the stomach frequently contain foreign material that can damage a gas analyzer.

A particular aspect of the invention involves the creation of a new and unique catheter via which the desired sample or samples can be obtained without the complications of prior techniques. One embodiment of the new and unique catheter comprises a catheter tube having a walled sampling chamber on the tube with the sampling chamber being in communication with the hollow interior of the tube. The wall of the sampling chamber comprises a material which is substantially impermeable to liquid yet is highly permeable to gas. One suitable material is polydimethylsiloxane elastomer.

In use the catheter is introduced into a patient to place the sampling chamber at a desired site within the organ of interest. An aspirating liquid fills the interior of the sampling chamber. The sampling chamber is left in place at the desired sampling site long enough to allow the gases present to diffuse through the wall of the sampling chamber into the aspirating liquid. The time should be long enough for the gases to equilibrate. The liquid impermeable nature of the sampling chamber wall material prevents both the aspirating liquid from leaking out of the chamber and also the intrusion of any liquids into the aspirating liquid. After the appropriate amount of placement time has elapsed the aspirating liquid is aspirated along with the gases which have diffused into it. The sample thus obtained is analyzed for gas content, in particular for $pCO_2$. In this way the $pCO_2$ within the lumen of the gut can be reliably measured with the fluid being free from lumenal debris.

In carrying out the diagnostic method of the invention the $pCO_2$ measurement is utilized in conjunction with a measurement of the bicarbonate concentration in an arterial blood sample of the patient for determining the pH of the tract wall.

Depending upon the particular condition of a given patient, the catheter may be left in place and samples may be taken at periodic intervals so that pH values may be periodically calculated. The procedure has a high reliability in accurately diagnosing intestinal ischemia in its incipient stages and such detection can be useful in treating the patient so that the potentially devastating consequences resulting from less timely detection may often be avoided.

The invention has applicability to many hollow internal organs although in the techniques described in detail herein the invention involves diagnosis within the gastrointestinal tract system. Depending upon the particular site or sites of interest within a patient, different types of catheters embodying principles of the invention may be appropriately used. One embodiment involves a catheter as described above. In that embodiment the catheter has a single sampling chamber and a single walled tube. Another embodiment contemplates the use of multiple individual single sampling chamber catheters of varying lengths bundled together to form a multiple sampling site catheter. Still another embodiment involves the use of a sump-type nasogastric tube. Yet another embodiment comprises a pliable catheter with a mercury bag at its end which may be used for certain procedures. In use of an embodiment that employs multiple sampling chambers, the pH in intestinal mucosal tissue at one site may be calculated and compared with the calculated pH values at other sites. This analysis can be a useful diagnostic aid to the attending physician. In the case of an abdominal aortic resection a multiple sampling chamber type catheter may be placed intralumenally in series in the colon at the time of the resection, and it may be used to aid in the early detection of colonic ischemia that occurs insidiously in approximately five percent of the patients subjected to this major operation. A multiple sampling chamber embodiment may also be introduced into the small intestine to monitor the pH and hence perfusion of the gut in patients with low flow states. In critically ill patients who require a nasogastric tube, a single sampling chamber embodiment may be incorporated into a conventional nasogastric tube and placed in the patient's stomach.

It is further contemplated that the invention may be practiced in connection with diagnosis of the biliary tract, urinary tract and pancreas for monitoring pH and hence perfusion of the associated organs.

In connection with this invention, a preliminary novelty search developed the following U.S. Pat. Nos. 2,470,665; 3,227,154; 3,548,805; 3,572,315; 3,952,730; and 4,168,703, none of which are deemed pertinent to the claims of the present invention.

The foregoing features and benefits of the invention in its several aspects, along with additional features and benefits, will be seen in the ensuing description and claims which should be considered in conjunction with the accompanying drawings. The drawings disclose presently preferred embodiments of catheters which embody principles of the invention and are used in the diagnostic aspects of the invention.

DESCRIPTION OF THE PREFERRED EMBODIMENT

Figure 1:
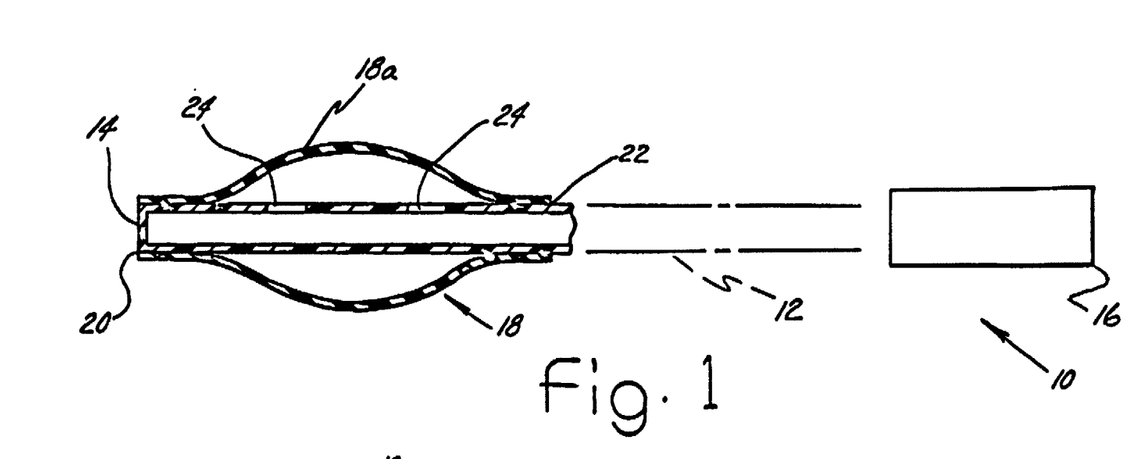
FIG. 1 is a diagrammatic view of a catheter embodying principles of the invention.

FIG. 1 illustrates a first embodiment of catheter 10. The catheter comprises a length of suitable tubing 12 one end 14 of which is closed, and the opposite end of which contains a connector such as a luer-lock 16 or equivalent. A sampling chamber 18 is provided on the tube adjacent the closed end 14.

The illustrated embodiment utilizes a tubular element 18a forming the sampling chamber wall. The preferred form of tubular element is polydemethylsiloxane elastomer. The tubular element has an internal diameter which allows it to be fitted over the tubing 12. The axial and segments of the tubular element 18a are secured to the outer wall of tube 12 at the locations indicated by the reference numerals 20 and 22. The attachment may be made in any suitable fashion with adhesive being a suitable attachment medium. Thus, the ends of the tubular element 18a are sealed in a closed relationship to the outer wall of the tube 12 thereby forming the sampling chamber 18 adjacent tube end 14. The wall material of the sampling chamber has a certain elasticity so as to allow the enclosure to assume a slightly ballooned or ovoidal shape when filled by aspirating liquid, as will be explained hereinafter.

Before the tubular element 18a is inserted over tube 12, suitable apertures 24 (shown on an enlarged scale in the drawing) are provided in the wall of tube 12 so that after assembly of the tubular element 18a the tube 12 the apertures 24 provide communication between the interior of tube 12 and the interior of the sampling chamber 18.

The material of the tubular element 18a possesses a characteristic whereby it is poorly permeable to liquid fluid while it is freely permeable to gaseous fluid. This property is important in practice of the invention. The material is also substantially impervious to the contents of the intestinal tract.

In one form of use the catheter is introduced into a patient by being fed into the colon from the anus and positioned intraoperatively. A suitable aspirating fluid, such as a saline solution, is introduced via the luer-lock 16, tube 12, and apertures 24 to fill the interior of the sampling chamber. The fluid passes through the apertures 24 filling the interior of the sampling chamber such that the sampling chamber assumes a balloon-like state.

According to the method of the invention the catheter is placed such that the sampling chamber is at a desired sampling site in the internal organ of interest. It is left at this site for a sufficient amount of time to allow gases, carbon dioxide being the particular gas of interest, to diffuse across the wall of the chamber into the aspirating liquid. Desirably the length of time should be sufficient to allow the gases to equilibrate. For example, one half hour may be suitable in certain applications.

The aspirating liquid containing the carbon dioxide gas is then withdrawn via the luer end lock 16. The aspirated sample thus obtained is subjected to analysis by a conventional gas analyzer to measure the $pCO_2$ content of the lumenal fluid. A measurement of the bicarbonate concentration in the arterial blood of the patient is also obtained. These two measurements are then used to calculate the pH of the tract. Measurements may be taken at periodic intervals in the same manner and in this way a record of pH values can be established.

The invention, in one respect, involves recognition of the principle that the partial pressure of gas in the lumen of the gastrointestinal tract is the same or very close to that in the wall of the gastrointestinal tract under a steady state condition and hence, can be used as a measure of the partial pressure of gas, especially $CO_2$, in the wall of that part of the gastrointestinal tract. The pH in the wall of the gastrointestinal tract can be calculated from this value if the bicarbonate concentration in arterial blood is also known. With the catheter of the invention the partial pressure of gas within the gastrointestinal tract can be readily measured because it allows a clear fluid sample, free of objectionable particulates and the like, to be obtained.

As explained earlier, a drop in the intramucosal pH has been found to accompany development of intestinal ischemia, and therefore the pH monitoring can be used to monitor for the incipiency of this potentially devastating condition. The earlier warning obtained with the invention offers the possibility of earlier treatment to counteract the condition.

Figure 2:
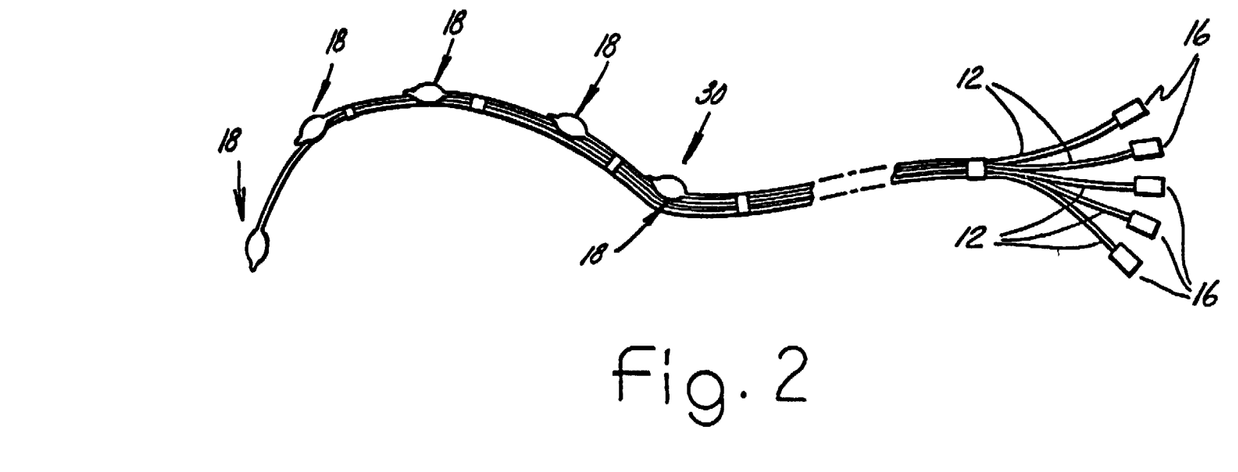
FIG. 2 is another embodiment of catheter embodying principles of the invention.

FIG. 2 illustrates a further embodiment of the catheter 30. This embodiment is also useful in the colon. The catheter 30 comprises multiple sampling chambers 18 at spaced locations along the length of the catheter. In this regard the catheter 30 is constructed as a bundle of individual catheters, such as the catheter 10 of FIG. 1, the individual catheters having various lengths. The illustrated example has five sampling chambers. This allows measurements to be taken at five different sites within the organ of interest and is useful for monitoring pH values not only in time at a particular sampling site but also in respect to concurrent pH measurements at different sites.

Figure 3:
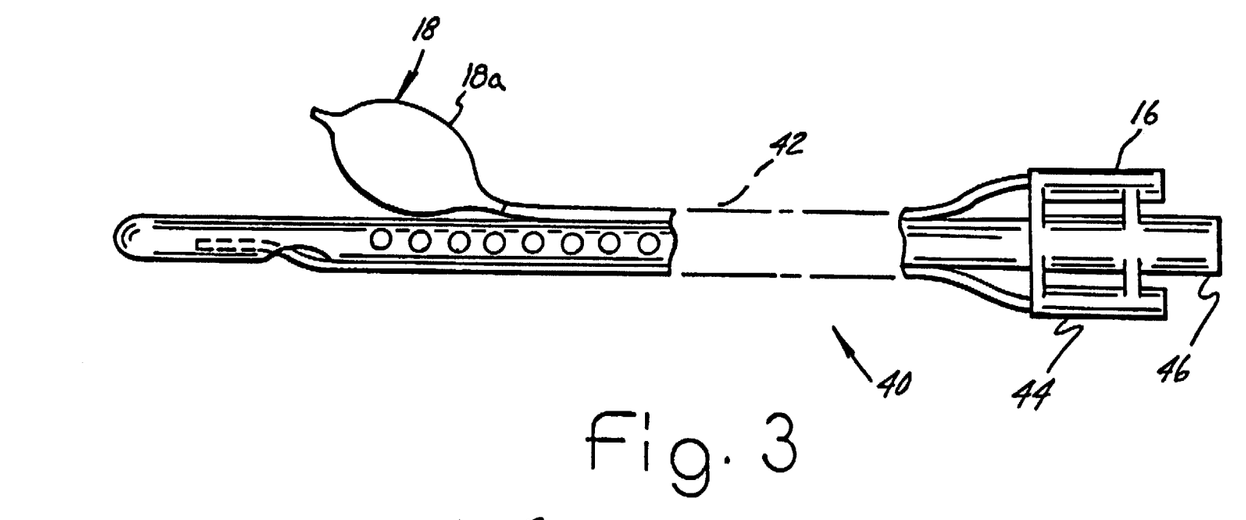
FIG. 3 is yet another embodiment of catheter embodying principles of the invention.

FIG. 3 illustrates a further embodiment of catheter 40 which comprises a tube 18a forming the wall of the sampling chamber; however, the tube 42 comprises a conventional double lumen nasogastric sump tube with a third lumen for the sampling chamber 18. The air and aspiration ports 44, 46 are of the nasogastric tube and the luer-end lock 16 is for the third lumen which leads to the sampling chamber 18. The catheter 40 is intended for use in the stomach. In this regard the catheter may be inserted into a patient in the same manner as a nasogastric tube, and the aspirating fluid for obtaining the $CO_2$ measurement is introduced and aspirated via luer lock 16 in the same manner as that for the previously described catheters.

Figure 4:
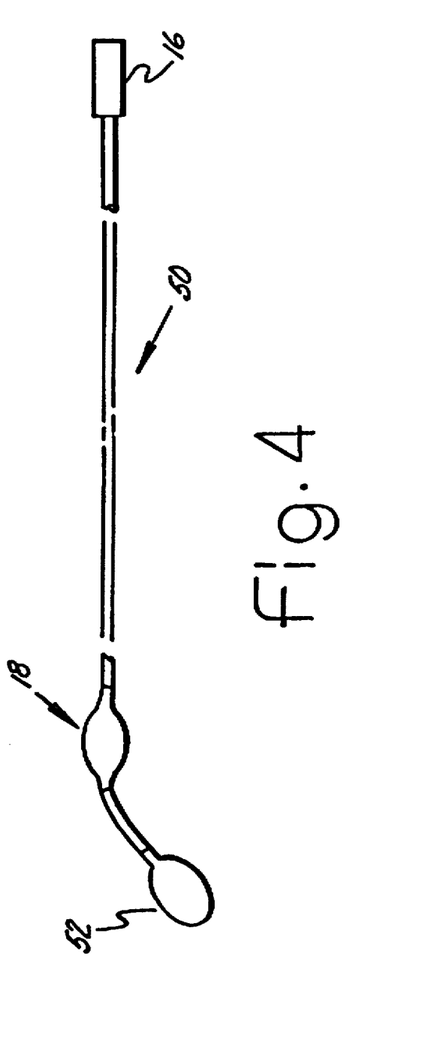
FIG. 4 is still another embodiment of catheter embodying principles of the invention.
Figure 5:
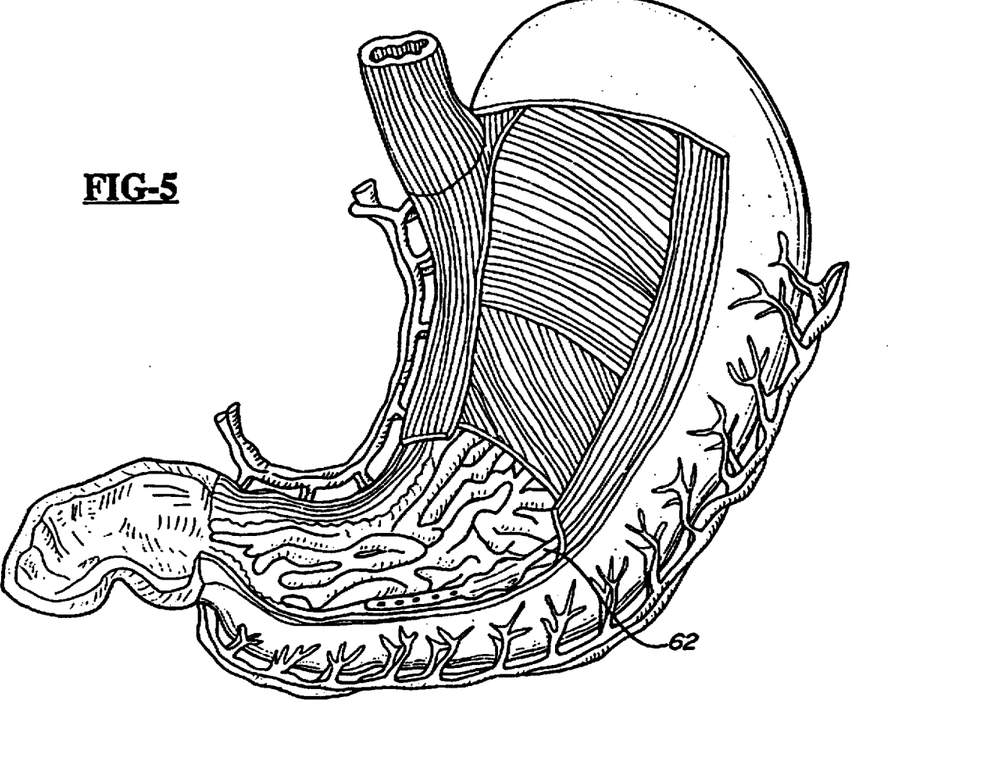
FIG. 5 is a detailed view illustrating the tonometric catheter in use within the stomach.
Figure 6:
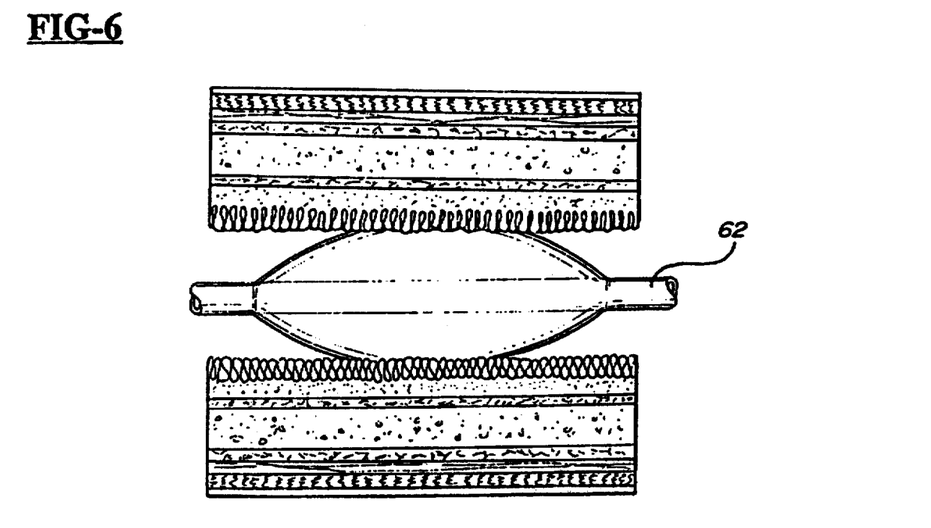
FIG. 6 is a detailed view illustrating the tonometric catheter in use within the colon.

FIG. 4 illustrates a still further embodiment of catheter 50 which is the same as the embodiment 10 of FIG. 1 except that the end 14 includes a sealed mercury bag 52. This catheter is intended for use in the small intestine, and it should be very soft and pliable with the mercury bag allowing peristalsis to position the tube in the small intestine. It should be long enough to reach the terminal ileum, and the same length as a colonoscope would be more than adequate.

If desired, any of the embodiments of single catheter may be bundled together as in the manner of FIG. 2 so as to provide multiple sampling sites in any catheter construction.

Desirably the volume of the sampling chamber should be relatively small in order to facilitate rapid equilibration of gas yet it must be large enough so that a suitable sample of about one milliliter for use in the gas analyzer can be withdrawn via the element 16. For example, around two milliliters is a suitable volume. The tubes such as the tube 12 should be of small caliber to insure as small a dead space as possible within the patient when in use. Tube 12 should also have as small a fluid volume (say about two-tenths milliliter) so that a minimum of aspirating liquid need be withdrawn at element 16 in advance of the sample from the chamber 18. The tube wall 12 should also be impermeable to gas. The luer end locks are conventional for connection to a syringe when aspirating fluid is to be introduced or withdrawn. The catheters may also contain rapid opaque markers for use in verifying position of the sampling chambers in the gut.

Where the catheter is to be left in the lumen of the gut for an extended period of time, for example several days, it should be soft enough to be allowed to remain in this position without damage to the wall of the gut. To facilitate insertion, for example into the colon, the catheter should be firm enough to allow for proper feeding. In this regard it may be appropriate to use a wire stent during insertion to facilitate positioning of the catheter with the wire stent being removed after proper positioning has been obtained.

While the preferred embodiment has been disclosed in connection with monitoring of the gastrointestinal tract it will be appreciated that its principles are applicable to other hollow internal organs to monitor pH and hence perfusion of those organs. Also while a preferred detailed construction for a catheter, such as described in FIG. 1, has been disclosed, it will be appreciated that other constructions may be developed which are equally as suitable. The disclosed construction however is presently preferred for the reason that it is readily fabricated using existing available materials. Other embodiments may include other, but equivalent materials for the sampling chamber wall. They may also differ in the specific fabrication details. As an example, the sampling chamber may be eccentric rather than symmetric about the tube 12.

It has now been further discovered that the pH of venous blood provides an excellent measure of the adequacy of tissue oxygenation of the whole body or organs, including solid organs, comparable to that achieved in hollow viscus organs by the method described herein, as well as that described in my co-pending and commonly assigned applications filed of even date herewith that relate to the use of a tonometric catheter to determine the adequacy of tissue oxygenation via the measurement of the pH of the wall of a hollow, viscus organ. See my co-pending and commonly assigned applications filed of even date herewith entitled "Remote Sensing Tonometric Catheter Apparatus and Method" and "Tonometric Catheter Combination", bearing respective Ser. Nos. 237,287 and 237,286; both completely and expressly incorporated herein by reference in toto.

For example, the methods of the present invention include the measure of the adequacy of whole-body oxygenation by measuring the pH of a central venous location. This may be done by tonometric sampling, or by the insertion of an electronic sensing means for measuring a fluid or gas property of the venous blood indicative of pH, or pH itself. This would include such means as a pH, $pCO_2$ or $pO_2$ electronic sensing means, such as a probe, placed into a central venous location. A tonometric catheter which includes a sampling chamber may also be employed. The sampling chamber is preferably constructed such that at least a portion of it is permeable to a gas or fluid property indicative of the pH of the venous blood in which it is placed. The sampling chamber of a tonometric catheter should also be impermeable to other materials that may interfere with the measurement of the desired gas or fluid property, such as other gases, proteins and the like. In a highly preferred embodiment, an ion-selective membrane is employed. The sampling chamber may optionally include a first non-temperature sensing means, and a second temperature sensing means, both in communication with said sampling chamber.

When no sensing means is employed, the tonometric catheter preferably employs a walled tonometric lumen, and said sampling chamber is in communication with said lumen. This provides the ability to carry out the aspiration of the sampling fluid or medium that is necessary when no remote sensing means is employed.

This method overcomes the problems associated with current methods of measuring whole-body oxygenation. Most methods currently employed to determine whole-body oxygenation include costly, time-consuming and error-prone measurements that typically include whole-body oxygen consumption and oxygen delivery. Another somewhat unreliable method currently employed is the frequently unreliable measurement of oxygen saturation in central venous blood.

The present method employing a central venous pH measurement overcomes many of the disadvantages of the currently art-employed methods; it has the additional advantage of being extremely reliable and relatively inexpensive.

This method is also useful in measuring the vitality or adequacy of tissue oxygenation for a specific solid internal organ, such as the brain, liver, kidney, or a limb, by measuring the pH of a venous vessel draining that organ or limb.

The insertion of a pH, $pO_2$ or $pCO_2$ catheter in the jugular, hepatic or renal veins, or any other regional vein draining a limb or the kidney, can be employed to measure the adequacy of tissue oxygenation in regional solid organs. A pH catheter and measurement is highly preferred.

Measurement of the adequacy of tissue oxygenation in the brain by the methods of the present invention is of particular interest because of the current lack of any art-disclosed or art-employed non-invasive, or minimally invasive, method of monitoring the adequacy of tissue oxygenation in this organ. The importance and significance of being able to make this measurement reliably and with minimum invasiveness and cost, especially in patient populations such as the elderly, patients having carotid artery surgery or patients with head trauma, with a reliable method cannot be over estimated.

In employing the methods of the present invention, the catheter may be inserted, for example, percutaneously into a jugular vein and advanced to monitor the venous drainage from the brain with great ease and minimal risk. Many patients in need of such measurements already have a catheter in the jugular vein for other non-pH central venous measurements. Other methods currently employed in clinical setting used to measure vitality of the brain, or the adequacy of its oxygenation or that of its tissue, include (1) EEG measurements which are cumbersome, difficult to interpret, and subject to electrical interference; (2) near-infrared-spectroscopy, which is costly, cumbersome and currently only applicable to neonates or premature babies with uncalcified skulls; (3) the Richmond-bolt, which requires that a hole be drilled into the skull and only measures pressure, thus providing no information about the adequacy of tissue oxygenation; and (4) NMR or nuclear magnetic resonance, which is still somewhat experimental, extremely costly and difficult to interpret. None of the above methods provide the precise information required to determine whether tissue oxygenation of the brain is adequate.

Measurement of the adequacy of tissue oxygenation in the liver is also of particular interest because of the importance of the liver in metabolizing drugs; the disturbance in drug metabolism precipitated by disturbances in hepatic perfusion; and because of the increasing frequency of liver transplants. For example, the measurements of pH in hepatic venous blood according to the instant invention provides a precise, reliable and relatively inexpensive method of monitoring the adequacy of hepatic oxygenation in all patents who are critically ill, including those having liver transplants. Other techniques that attempt to measure the vitality of adequacy of oxygenation of the liver include open biopsy of the liver. Some work has been attempted which involves intrahepatic tissue pH probes. The problem with tissue pH probes is the artefact created by the invasive insertion of the probe, and the difficulty of probe placement and of maintaining its position in the liver tissue as the liver moves with respiration. Measurements of hepatic venous pH according to the methods of the present invention do not have these shortcomings.

Accordingly, the present invention relates to a method for determining the vitality or adequacy of whole-body oxygenation of a human or other mammal in vivo comprising:

(i) providing a means for measuring a fluid or gas property indicative of pH, such as an arterial pH catheter, suitable for insertion into a central venous location;

(ii) inserting said means such as a pH catheter into a central venous location;

(iii) measuring the pH of the blood at said central venous location either directly or from the selected fluid or gas property; and (iv) determining the vitality or adequacy of whole-body oxygenation of said human or mammal from said pH measurement.

This method may also be employed to determine the vitality or adequacy of oxygenation of a solid internal organ. It therefore comprises the steps of:

(i) providing a means for measuring a fluid or gas property indicative of pH, such as an arterial pH catheter, suitable for insertion into a venous vessel at least partially draining an organ of interest;

(ii) inserting said means or catheter into said venous vessel draining said organ;

(iii) measuring the pH of the blood in said venous vessel, either directly or from the selected fluid or gas property; and (iv) determining the vitality or adequacy of oxygenation of said organ from said pH measurement.

While a preferred embodiment of the invention has been disclosed, it will be appreciated that principles of the invention, as set forth in the following claims, are applicable to other embodiments.

What is claimed is:

1. A tonometric catheter device comprising a catheter having a catheter tube; a walled sampling chamber on the tube in communication with the interior of the tube, said walled sampling chamber generally surrounding a portion of said catheter tube and sealingly interconnected therewith, the wall of said walled sampling chamber being composed of a deformable material which is freely permeable to one or more liquid fluids or gaseous fluids of interest, said fluids of interest including oxygen gases and carbon dioxide, said wall sampling chamber being inflated for forming an interior space between said walled sampling chamber and said catheter tube for selectively positioning a portion of said walled sampling chamber substantially in contact with a wall portion of a human internal organ at a desired sampling site therein in order to allow said fluids of interest to permeate from the tissue of the wall portion of the organ into said sampling chamber, said catheter being left disposed at the sampling site for a predetermined length of time sufficient to allow any of said fluids of interest present at the wall portion of the organ sampling site to permeate across the wall of said sampling chamber into said sampling chamber, and means for withdrawing at least a portion of said diffused fluids of interest.

2. A tonometric catheter device, comprising a catheter having a catheter tube; a walled sampling chamber on the tube in communication with the interior of the tube, said walled sampling chamber being defined by a balloon member generally surrounding a portion of said catheter tube and sealingly interconnected therewith, the wall of said walled sampling chamber being composed of a deformable material which is freely permeable to one or more liquid fluids or gaseous fluids of interest, said fluids of interest including oxygen gases and carbon dioxide; said balloon member being inflated for forming an interior space between said balloon member and said catheter tube for selectively positioning a portion of said balloon member substantially in contact with a wall portion of a human internal organ at a desired sampling site therein in order to allow said fluids of interest to permeate from the tissue of the wall portion of the organ into said sampling chamber; and means for withdrawing at least a portion of said diffused fluids of interest.

3. A tonometric catheter device comprising a catheter having a catheter tube; a walled sampling chamber on the tube in communication with the interior of the tube, said walled sampling chamber generally surrounding a portion of said catheter tube and sealingly interconnected therewith, the wall of said walled sampling chamber being composed of a deformable material which is freely permeable to one or more liquid fluids or gaseous fluids of interest, said fluids of interest including oxygen gases and carbon dioxide, said walled sampling chamber being inflated for forming an interior space between said walled sampling chamber and said catheter tube, substantially in contact with a wall portion of a human internal organ at a desired sampling site therein in order to allow said fluids of interest to permeate from the tissue of the wall portion of the organ into said sampling chamber, said catheter being left disposed at the sampling site for a predetermined length of time sufficient to allow any of said fluids of interest present at the wall portion of the organ sampling site to permeate across the wall of said sampling chamber into said sampling chamber.

* * * * *